United States Patent [19]

Granzow et al.

[11] E Patent Number: Re. 32,056

[45] Reissued Date of Patent: Dec. 24, 1985

[54] METHOD OF FORMING A CONNECTION BETWEEN TWO SEALED CONDUITS USING RADIANT ENERGY

[75] Inventors: Daniel B. Granzow, Ingleside, Ill.; Garry L. Carter, Racine, Wis.; David W. Ammann, Longmount, Colo.

[73] Assignee: Baxter Travenol Laboratories, Inc., Deerfield, Ill.

[21] Appl. No.: 271,907

[22] Filed: Jun. 9, 1981

Related U.S. Patent Documents

Reissue of:

[64] Patent No.: 4,157,723
Issued: Jun. 12, 1979
Appl. No.: 843,608
Filed: Oct. 19, 1977

[51] Int. Cl.[4] ..... B65B 3/04

[52] U.S. Cl. ..... 141/1; 128/760; 141/311 R; 156/272.2; 156/304.6; 250/432 R

[58] Field of Search ..... 141/1, 98, 114, 311 R, 141/382-388, 392; 222/541; 285/3, 4, 67; 156/272, 289, 272.2, 304.6, 272.4, 272.8; 219/85 BA, 349, 85 BM, 354; 250/432; 128/362, 760; 220/89 B

[56] References Cited

U.S. PATENT DOCUMENTS

| | | | |
|---|---|---|---|
| 998,507 | 6/1911 | Hasty . | |
| 1,010,626 | 12/1911 | Hasty . | |
| 1,151,300 | 8/1915 | Soresi . | |
| 1,292,603 | 1/1919 | Hohman . | |
| 1,313,225 | 8/1919 | Gootee . | |
| 1,921,809 | 8/1933 | Crain . | |
| 2,507,379 | 5/1950 | Morrison . | |
| 2,553,259 | 5/1951 | Hagedom | 156/272.2 X |
| 2,622,053 | 12/1952 | Clowe et al. | 156/272.2 X |
| 2,729,221 | 1/1956 | Gorham et al. . | |
| 2,744,432 | 12/1956 | Danziger . | |
| 2,782,496 | 2/1957 | Augustauskas . | |
| 2,839,788 | 6/1958 | Dembiak . | |
| 2,903,004 | 9/1959 | Gerteis . | |
| 2,910,083 | 10/1959 | Cook . | |
| 2,933,333 | 4/1960 | Bredtschneider et al. . | |
| 2,958,545 | 11/1960 | Stelzer . | |
| 2,998,018 | 8/1961 | Beck et al. . | |
| 3,023,762 | 3/1962 | Cook . | |
| 3,052,253 | 9/1962 | Priaroggia et al. . | |
| 3,084,705 | 4/1963 | Feuer . | |
| 3,214,502 | 10/1965 | Schaar . | |
| 3,244,412 | 4/1966 | Robinson et al. . | |
| 3,285,627 | 11/1966 | Kozulla et al. . | |
| 3,384,526 | 5/1968 | Abramson et al. | 219/349 X |

(List continued on next page.)

FOREIGN PATENT DOCUMENTS

| | | |
|---|---|---|
| 2452858 | 5/1975 | Fed. Rep. of Germany . |
| 2639584 | 4/1977 | Fed. Rep. of Germany . |
| 2331687 | 9/1977 | Fed. Rep. of Germany . |
| 801162 | 11/1955 | United Kingdom . |
| 1027528 | 4/1966 | United Kingdom . |
| 1428391 | 3/1976 | United Kingdom . |

OTHER PUBLICATIONS

Van Nostrand's Scientific Encyclopedia, 1968, pp. 582, 583, 1458 and 1459.

Webster's New Collegiate Dictionary, 1979, p. 583.

The International Dictionary of Physics, 1961, pp. 239-241.

(List continued on next page.)

*Primary Examiner*—Frederick R. Schmidt

*Attorney, Agent, or Firm*—Daniel D. Ryan; Paul C. Flattery; Bradford R. L. Price

[57] ABSTRACT

A connection may be formed between sealed conduits in which each conduit carries an opaque, thermoplastic wall portion preferably having a melting range above essentially 200° C., preferably with the opaque thermoplastic wall portions being carried on the conduit about their periphery by transparent wall portions of the conduit. The opaque wall portions of the conduits are brought together into facing contact, and then exposed to sufficient *electromagnetic* radiant energy to cause the opaque wall portions to fuse together, and to open an aperture through the fused wall portions. This provides sealed communication between the interiors of the conduits.

54 Claims, 5 Drawing Figures

U.S. PATENT DOCUMENTS

| | | | |
|---|---|---|---|
| 3,391,951 | 7/1968 | Miller . | |
| 3,404,051 | 10/1968 | Hall . | |
| 3,410,979 | 11/1968 | Larsson . | |
| 3,466,065 | 9/1969 | Acker et al. . | |
| 3,493,002 | 2/1970 | Brugler . | |
| 3,549,451 | 3/1966 | Krugler . | |
| 3,588,440 | 6/1971 | Morse . | |
| 3,616,024 | 10/1971 | Windle . | |
| 3,640,790 | 2/1972 | Rowley et al. . | |
| 3,812,659 | 5/1974 | Westergren et al. . | |
| 3,865,411 | 2/1975 | Rowe et al. . | |
| 3,902,489 | 9/1975 | Carter . | |
| 3,909,910 | 10/1975 | Rowe et al. . | |
| 3,913,348 | 10/1975 | Magester . | |
| 3,941,641 | 3/1976 | Heller, Jr. et al. | 156/272.2 |
| 3,968,195 | 6/1976 | Bishop . | |
| 3,977,385 | 12/1976 | Osborne | 156/272.8 |
| 3,986,508 | 10/1976 | Barrington . | |
| 4,004,586 | 1/1977 | Christensen et al. . | |
| 4,019,512 | 4/1977 | Tenczar . | |
| 4,022,205 | 5/1977 | Tenczar . | |
| 4,022,256 | 5/1977 | Berkman et al. . | |
| 4,030,494 | 6/1977 | Tenczar . | |
| 4,139,005 | 2/1979 | Dickey | 220/89 B |
| 4,177,372 | 12/1979 | Kotera et al. . | |

OTHER PUBLICATIONS

DHEW Publication No. (NIH) 76-1004, "Frozen Red Cell Outdating", Mar. 14, 1975, Bethesda, Maryland, pp. 43-51.

B. A. Myhre et al., "An Aseptic Fluid Transfer System for Blood and Blood Components", Transfusion, Sep-.-Oct., 1978, pp. 546-553.

F. J. Tenczar, Transfusion, Sep.-Oct. 1976, pp. 477-482, entitled "Sterile Connector".

William W. Cooper et al., pp. 31-41 of DHEW Publication No. (NIH 76-1004, Mar. 14, 1975, entitled, "A Two-Stage Heat Sterilizable Connector For Use In Processing Frozen Blood".

R. E. Trotman, "Sterilization by Radio Frequency Induction Heating: A Method for the In Situ Sterilization of Vessels in Automatic Bacteriological Apparatus", Journal of Applied Bacteriology 32, pp. 2, 9, 7-300, (1960).

METHOD OF FORMING A CONNECTION BETWEEN TWO SEALED CONDUITS USING RADIANT ENERGY

Matter enclosed in heavy brackets [ ] appears in the original patent but forms no part of this reissue specification; matter printed in italics indicates the additions made by reissue.

BACKGROUND OF THE INVENTION

The need to form a sterile, sealed connection between a pair of conduits arises particularly in the field of blood and blood component handling, as well as in other areas where a sterile connection between containers is desired.

In the blood handling field, it may be desired to make use of only one half of a unit of blood in a bag or the like. When this happens, it is customary to discard the nonused portion of the blood unit within a day after the access to the bag was made, even when efforts are made to maintain sterility by using conventionally accepted aseptic methods of access to the blood bag. This is so because only one or two air-borne bacteria could multiply in the stored blood to create the danger of septicemia, if the bacteria were allowed to multiply over a period of more than a very few hours, and the blood was then administered to a patient.

Accordingly, to eliminate the need for disposing of the remainder of a unit of blood when only a partial unit is needed, or for the many other reasons why sealed, sterile access between various containers would be desired, a considerable amount of research has taken place in developing aseptic fluid transfer systems. For example, Berkman, et al. U.S. Pat. No. 4,022,256, discloses a sterile connection means in which a heat-fusable tube carries an inner layer of plastic material which is nonmeltable at the temperature used. An allegedly-sterile connection is made by the use of a heating die pressing the nonmeltable layer through the melting outer layers of the tube, to provide a sterile connection between the two tubes, with the melted layers of the tube forming a single, perforated layer.

The invention of the Berkman patent requires a special heating die to press the nonmelting layer of material through the meltable layers of the conduits. Also, in the embodiment shown in the Berkman patent, the meltable material presses against the heating die. Any adhesion of the meltable material to the heating die when the die is pulled apart after the pressing step could cause the connection to rip open, or at least be seriously weakened.

In accordance with this invention, the use of a heating and pressing die for obtaining a sterile connection between two conduits is eliminated. Instead, *electromagnetic* radiant energy is used to selectively melt a portion of the conduit wall without providing any physical contact of a die or the like to the melting portion. Also, in this invention, mechanical connection means may be provided between the two conduits to protect the fused, sterile connection area from being mechanically ripped apart.

DESCRIPTION OF THE INVENTION

In accordance with this invention, a connection, and particularly a sterile connection, may be formed between sealed conduits. Each conduit carries a thermoplastic wall portion preferably having a melting temperature of at least essentially 200° C., and which is opaque to the particular radiant energy intended for use herein. Such melting temperature, which may be a range of temperatures, may be determined, for example, by differential thermal analysis.

To make the sterile connection, the opaque wall portions of the conduits are brought together into facing contact. The opaque wall portions are exposed to sufficient *electromagnetic* radiant energy to cause them to fuse together, and to open an aperture through the fused wall portions. This provides sealed communication between the interiors of the conduits.

Preferably, the opaque thermoplastic wall portions are carried about their peripheries by a transparent, rigid housing which typically defines the end of a conduit. The remainder of the conduit may be flexible, if desired. The rigid housing is transparent, and is made of a material which is not materially softened under the specific *electromagnetic* radiant energy conditions used in the process. Instead, the *electromagnetic* radiant energy can pass through the transparent housing, which preferably surrounds and protects the opaque wall portions as they are placed together in facing contact, so that primarily it is the opaque facing wall portions that are heated to their melting point rather than the transparent housing, which supports and protects the opaque wall portions.

As the opaque wall portions melt, they preferably fuse together into a single sealed mass, and, due to the melting, a central aperture is formed in the melted, opaque, thermoplastic wall portion. Any bacteria residing upon the exterior surfaces of the opaque wall portions are entrapped in the melted mass and preferably killed by exposure to the melting temperature of the opaque wall portions, which melting temperature is preferably on the order of 220° to 250° C.

The *electromagnetic* radiant energy can be provided to the system by means of visible, infrared, ultraviolet, or radio frequency energy as may be desired. The term "opaque" implies that the opaque wall portions are adapted to absorb a high percentage of the particular *electromagnetic* radiant energy to which it is exposed. The term "transparent" implies that a lower percentage of the *electromagnetic* radiant energy applied is absorbed. Focused, infrared radiant energy is particularly desirable for use.

Lasers may also be used as desired to provide the *electromagnetic* radiant energy.

The opaque wall portions may be prestressed by uniaxial or biaxial orientation, or with radial stress patterns, to facilitate the formation of the central aperture as the opaque wall portions seal together. Also, unstressed wall portions may be used, with the central aperture formation taking place by cohesion.

Referring to the drawings, FIG. 1 is an elevational view of a pair of conduit ends, the other ends of which may be connected to a pair of blood bags or the like, each terminating in a pair of housings which carry an opaque, thermoplastic wall portion in accordance with this invention.

Figure 1:
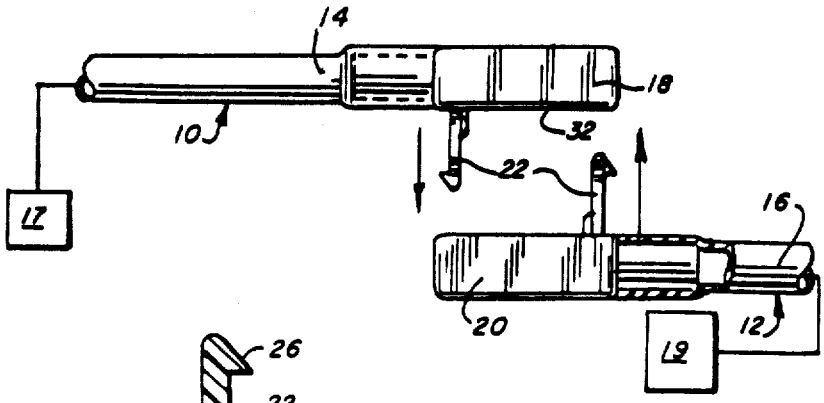
Figure 2:
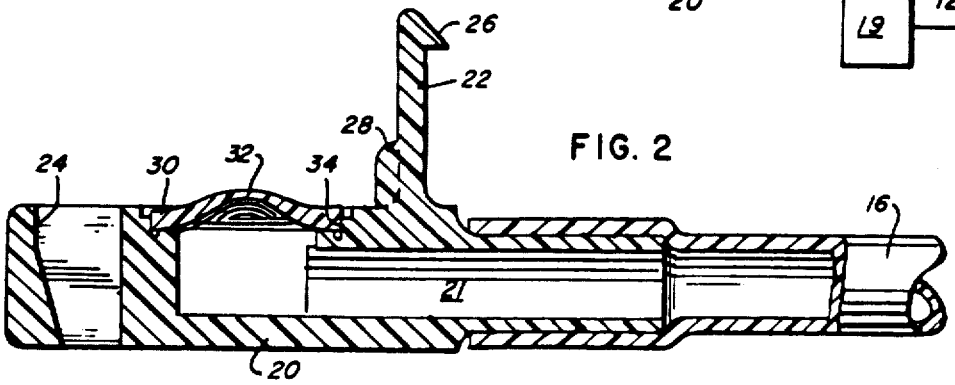
FIG. 2 is an enlarged view, taken partly in longitudinal section, of one of the conduit ends as shown in FIG. 1.
Figure 3:
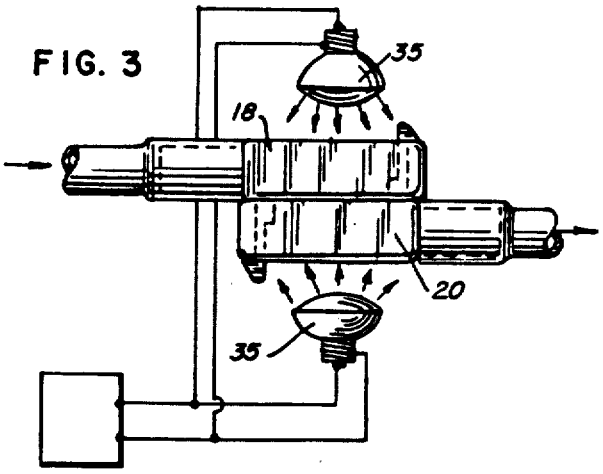
FIG. 3 is an elevational view showing the two conduit ends of FIG. 1 after they have been joined together to bring the opaque wall portions into facing contact, further showing schematically the step of exposing the opaque wall portions to sufficient *electromagnetic* radiant energy to cause them to fuse together and open an aperture.
Figure 5:
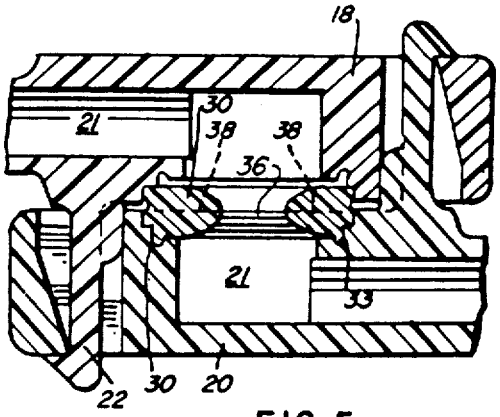
FIG. 5 is an enlarged, longitudinal sectional view of a portion of the structure of FIG. 3, taken after the step of exposure to *electromagnetic* radiant energy.

Referring to the drawings, conduits 10,12, are shown to include flexible sections 14, 16, one end of each which may be connected to a conventional blood bag 17, 19 or other container.

Housings 18, 20 are shown being made of a transparent, high melting plastic material such as Lexan, a polycarbonate material sold by General Electric. Each housing defines a hollow interior chamber 21 in communication with the bore of tubes 14 or 16, plus a bayonet member 22 and a slot 24. Both bayonet 22 and slot 24 are positioned asymmetrically on the housing so that each bayonet 22 can fit into a corresponding slot 24 of an identical housing in a generally permanent, snap-fit relation. Each bayonet 22 may be retained in slot 24 by the hooking action of barbs 26.

Accordingly, upon connection of a pair of housings 18, 20, they are only disconnected again with a great deal of effort. Preferably, enlarged portions 28 of each bayonet 22 are proportioned to bear against the inner wall of the slot 24 of the mating housing, to make the disconnection of the housings yet more difficult by reducing the capability of bayonets 22 to flex rearwardly.

Each housing 18, 20 carries an opaque wall portion 30, which may be made out of a thermoplastic material having a melting temperature of preferably at least 200° C.

For example, polycarbonate materials such as Lexan may be used, or polysulfone material such as Union Carbide's Udel or Radel. Also, polyethersulfone materials may be used.

The thermoplastic opaque wall portion 30 generally contains a filler such as carbon black to render it opaque, although other desired fillers which are absorbent of the type of *electromagnetic* radiant energy to be used may be provided as a substitute for carbon black, for example, iron oxide, manganese dioxide, or the like.

Figure 4:
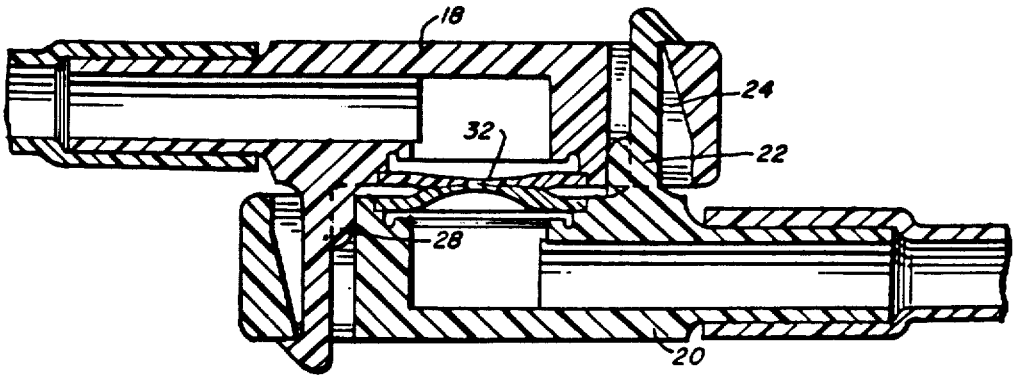
FIG. 4 is an enlarged view, taken in longitudinal section, of the structure of FIG. 3 prior to the step of exposure to *electromagnetic* radiant energy as described above.

Opaque, thermoplastic wall portion 30 is shown to be a disc which is preferably thinner at its central portion 32 than at its peripheral portions. Disc 30 may be retained by ultrasonic sealing or the like about its periphery to its housing in a recess 34 thereof, and is shown to bulge slightly outwardly, to facilitate good, pressurized contact between facing pairs of opaque wall portions, as shown in FIG. 4. Annular groove 33 provides room for the plastic of wall portion to flow as the opaque disc is assembled into the transparent housing.

FIG. 4 also shows how bayonets 22 fit into the opposed slots 24 of the mating housings, to provide permanent connection between the respective housings, with the opaque wall portions 30 being pressed together, and surrounded in protective manner by the respective housings.

After housings 18, 20 have been connected, they are irradiated with *electromagnetic* radiant energy of a type which is absorbed by the particular opaque wall portions used. Specifically, infrared radiations is one preferred form of *electromagnetic* radiant energy. It may be provided, for example, by the use of two 150 Watt Sylvania lamps *35* with elliptical reflector type (model DJL). This provides focused, infrared light which can be focused at the centers of abutting wall portions 30 to rapidly heat them over a period of preferably ten to twenty seconds to essentially the melting point, resulting in the fusing of the respective wall portions 30 together, and the formation of aperture 36, by relief of stress or by simple cohesive forces, through wall portions 30.

Bacteria trapped on the wall portion are killed by heating of wall portion 30 to its melting temperature, and are further entrapped upon rehardening of the melted material of wall portions 30. This results in the formation of a connection between the sterile flow channels 21, while the continued maintenance of sterility in the channels is assured.

The fused wall portions 30 fuse together to form a hermetic seal about aperture 36, to prevent a break in the sterility of the flow path. At the same time, the seal line 38 between the respective membrane wall portions 30 is protected from mechanical rupture by the generally permanent connection between respective housings 18, 20.

Alternatively, if it is desired to utilize radio frequency eneregy or the like as the *electromagnetic* radiant energy, opaque wall portions 30 may be made out of a plasticized polyvinylchloride, while the remainder of housings 18, 20 may be made of a plastic material which is relatively inert to R.F. energy, for example polypropylene, polyethylene, or a similar material which does not heat significantly when it is exposed to radio frequency or other high energy, high frequency radiant electrical fields.

Accordingly, by this invention a sterile connection can be made, for example, between a full and an empty blood bag by simply connecting a conduit from each of the bags which carries a respective housing 18, 20 in accordance with this invention. The connected housings can be briefly exposed, for example for about fifteen seconds to focused infrared radiation, to melt the opaque wall sections, fusing them together and forming an aperture through the sections. The sterile connection is thus achieved, through which a portion of the blood of the full blood bag can be passed to the empty bag for use. Thereafter, the bags may be disconnected in conventional manner by heat sealing one or both of the flexible conduits 14, 16 leading from the blood bag to the housings 18, [29] *20* in a HEMATRON® heat sealer, sold by the Fenwal Division of Baxter Travenol Laboratories, Inc. Then the blood bags may be conveyed to their desired site of use, or back to long-term storage.

The above has been offered for illustrative purposes only, and is not intended to limit the scope of the invention of this application, which is as defined in the claims below.

That which is claimed is:

1. The method of forming a connection between sealed conduits, each conduit carrying an opaque, thermoplastic wall portion, which method comprises:

bringing said opaque wall portions of said conduits together into facing contact, and [exposing said opaque wall portions to sufficient] *applying sufficient electromagnetic* radiant energy to cause said opaque wall portions to fuse together and to open an aperture through said fused wall portions, providing sealed communication between the interiors of said conduits.

2. The method of claim 1 in which said opaque, thermoplastic wall portions are carried about their peripheries on said conduits by transparent, rigid housing portions of said conduits.

3. The method of claim 2 in which the interiors of said conduits are sterile.

4. The method of claim 3 in which the melting temperature of said thermoplastic wall portion is at least 200 degrees C.

5. The method of claim 4 in which said housing portion defines means for generally permanent connection with an identical housing portion in a position to bring the respective opaque wall portions of said housing portions together into facing contact, to protect the fused, opaque wall portions from mechanical stress.

6. The method of claim 5 in which said *electromagnetic* radiant energy is infrared radiation.

7. The method of claim 6 in which [the opaque, thermoplastic wall portions are exposed to] said infrared radiation *is applied* for ten to twenty seconds.

8. A connector member for providing sealed sterile connection between containers, which connector member comprises a hollow, transparent housing adapted for connection to a first container, the hollow interior of said housing member being sealed from the exterior by housing walls, some of said housing wall comprising an opaque wall portion separating the hollow housing interior from the exterior, said opaque wall portion being sealed to the remainder of the transparent housing, said opaque wall portion being made of a thermoplastic material, and means for connecting said housing to a corresponding second, hollow, transparent, sealed housing which carries, as a part of [a] *the* second housing[,] walls separating the second housing interior from the exterior, *a* second opaque wall portion, said connection between the respective housings being adapted to bring the respective opaque wall portions together into facing contact, said opaque wall portions being adapted to facilitate the opening of an aperture upon heating said wall portions to the melting temperature by [means] *the application* of *electromagnetic* radiant energy.

9. The sterile connection member of claim 8 in which said transparent housing defines an asymmetrically positioned bayonet member and an asymmetrically positioned slot member, said bayonet member being adapted to pass into a corresponding slot member of said second housing and said slot member being proportioned to receive a corresponding bayonet member from said second housing, to provide generally permanent connection between said housings.

10. The connector member of claim 9 in which said bayonet member carries a barb on one side thereof, and a reinforcement member is provided to restrict the movement of said bayonet member in the direction away from said one side.

11. The connector member of claim 10 in which said opaque, thermoplastic wall portion is made of material having a melting temperature of at least 200 degress C.

12. The connector member of claim 11 in which said transparent housing is in sealing communication with the end of flexible tubing for connection to a medical liquid container.

13. A blood bag which carries the connector member of claim 12.

14. A connector member which comprises first and second hollow, transparent, generally rigid housings connected in sealed, communicating relation with the ends of hollow, flexible tubing, the walls of said housings sealing the hollow interiors thereof from the exterior except through said flexible tube, a portion of each of the housing member walls comprising *an* opaque wall [portions] *portion* sealed to the remainder of said transparent [housings] and in abutting contact with each other, said opaque wall [portions] *portionof said first housing* being adapted to be brought into abutting relation with [an] *said* opaque wall portion of [a similar connector member] *said second housing* and adapted to facilitate the opening of an aperture through said abutting opaque wall portions upon heating said wall portions to the melting temperature by [means] *the application* of *electromagnetic* radiant energy.

15. The connector member of claim 14 in which said opaque thermoplastic wall portions are made of a material having a melting temperature of at least 200 degrees C.

16. The connector member of claim 15 in which each transparent housing defines an asymmetrically positioned bayonet member and an asymmetrically positioned slot member, each bayonet member passing through the corresponding slot member of the other housing in retaining relationship thereto, to provide generally permanent connection between said housings.

17. The connector member of claim 16 in which each bayonet carries a barb on one side thereof, and a reinforcement member is provided to restrict the movement of said bayonet member in the direction away from said one side.

18. The connector member of claim 17 in which said opaque wall portions are stressed to facilitate the opening of an aperture through said wall portions upon heating said opaque wall portions to the melting temperature by [means] *the application* of *electromagnetic* radiant energy.

19. The connector member of claim 8 in which said opaque wall portions are stressed to facilitate the opening of an aperture through said wall portions upon heating said opaque wall portions to the melting temperature by [means] *the application* of *electromagnetic* radiant energy.

20. The method of opening a connection between sealed conduits within a transparent housing, said conduits being separated by opaque wall means positioned within said housing, comprising [exposing said opaque wall means to a source of] *applying electromagnetic* radiant energy *from a source* positioned outside of said transparent housing of an intensity and duration sufficient to cause said opaque wall means to fuse and to open an aperture therethrough, providing communication between the interiors of said sealed conduits.

21. The method of forming a connection between sealed conduits in which each conduit is positioned within a separate, generally transparent housing which carries an opaque wall portion separing the interior of said housing from the exterior, which method comprises:

bringing the opaque wall portions of the housing into facing contact, in which the facing opaque wall portions are surrounded by the respective housings, and [exposing said opaque wall portions to sufficient] *applying sufficient electromagnetic* radiant energy to cause said opaque wall portions to fuse together and to open an aperture through said fused wall portions, providing sealed communication between said conduits.

22. The method of claim 21 in which said opaque wall portions are made of a thermoplastic material, and are attached about their peripheries to said transparent housings, the *electromagnetic* radiant energy being adapted to pass through said transparent housings to said opaque wall portions.

23. The method of claim 22 in which the melting range of said thermoplastic wall portions includes a temperature of at least 200° C.

24. The method of claim 23 in which each generally transparent housing defines means for generally permanent connection with an identical housing in a position to bring the respective opaque wall portions of said housings together into said facing contact, to protect the fused opaque wall portions from a mechanical stress.

25. The method of claim 24 in which said *electromagnetic* radiant energy is infrared radiation.

26. A connector member for providing sealed connection between a pair of conduits which comprises transparent housing means enclosing a portion of said pair of conduits, and opaque wall means positioned within said housing means in communication with and to separate the respective conduits, said opaque wall means being adapted to facilitate the opening of an aperture upon heating said opaque wall means to the melting temperature by [means] *the application* of *electromagnetic* radiant energy.

27. A connector member for providing sealed, sterile connection, said connector member comprising a pair of hollow, transparent housings, the hollow interiors of each of said housings being sealable from the exterior, some of the walls of each housing comprising an opaque wall portion separating the hollow housing interior from the exterior, said opaque wall portions being sealed to the remainder of said transparent housing, and means for connecting said housings together, said connection between the respective housings being adapted to bring the respective opaque wall portions together into facing contact, the opaque wall portions being adapted to facilitate the opening of an aperture upon heating said opaque wall portions to the melting temperature by [means] *the application* of *electromagnetic* radiant energy to fuse said opaque wall portions together to provide a connection between the interiors of the respective housings.

28. The connector member of claim 8 in which said thermoplastic material from which the opaque wall portions is made is a filled organic plastic formulation.

*29. A member comprising body means attachable to the end portion of a conduit, said body means being made of a material which is generally transparent to the passage of electromagnetic radiant energy, and means defining a meltable wall sealingly disposed on said body means and being made of a material which is generally opaque to the passage of electromagnetic radiant energy for normally sealing the conduit from communication with the atmosphere and for forming, in response to the application of electromagnetic radiant energy to melt said wall, an opening in said wall.*

*30. A member according to claim 29*

*and further including means for bringing said meltable wall into facing contact with a corresponding meltable wall of a second member as defined by claim 29, and*

*wherein said opening in each of said meltable walls which is formed in response to said application of eletromagnetic radiant energy is disposed generally along the point of facing contact between said meltable walls.*

*31. A member comprising body means attachable to the end portion of a conduit and being made of a material which is generally transparent to the passage of infrared radiation, and means defining a meltable wall sealingly disposed on said body means and being made of a material which is generally opaque to the passage of infrared radiation for normally sealing the conduit from communication with the atmosphere and for forming, in response to the application of infrared radiation to melt said wall, an opening in said wall.*

*32. A member according to claim 31*

*wherein the opaque material of said meltable wall is black in color.*

*33. A member according to claim 31*

*and further including means for bringing said meltable wall into facing contact with a corresponding meltable wall of a second member as defined in claim 32, and*

*wherein said opening in each of said meltable walls which is formed in response to said application of infrared radiation is disposed generally along the point of facing contact between said meltable walls.*

*34. A member according to claim 30 or 33*

*wherein said meltable wall includes at said point of facing contact a generally outwardly bowed portion to facilitate said facing contact.*

*35. A member according to claim 29 or 31*

*wherein said body means includes body wall means defining a hollow interior adapted for communication with the conduit end portion, and*

*wherein said meltable wall extends in said hollow interior and is operative for normally sealing said hollow interior, and thus said conduit end portion, from communication with the atmosphere.*

*36. A member according to claim 35*

*wherein said body means includes passage means communicating with said hollow interior and adapted for attachment to the end portion of the conduit.*

*37. A member according to claim 35*

*wherein said meltable wall includes a disc-shaped member having a center portion which is thinner than its peripheral portions.*

*38. A member according to claim 37*

*wherein said meltable wall is sealed about said peripheral portions to said body wall means.*

*39. A member according to claim 29 or 31 wherein said meltable wall is made of material having a melting temperature of at least 200°C.*

*40. A member according to claim 39 wherein said meltable wall is made of thermoplastic material.*

*41. A member comprising body means being made of a material which is generally transparent to the passage of electromagnetic radiant energy and which defines a fluid passage attachable to a conduit for normally sealing the conduit from communication with the atmosphere and including means for forming on said body means a meltable surface made of a material which is generally opaque to the passage of electromagnetic radiant energy, said means being further operative for creating in response to the application of electromagnetic radiant energy to melt said surface, an opening in said body means through said surface.*

*42. A member comprising body means being made of a material which is generally transparent to the passage of infrared radiation and defining a fluid passage attachable to a conduit for normally sealing the conduit from commu-*

*nication with the atmosphere and including means for forming on said body means a meltable surface being made of a material which is generally opaque to the passage of infrared radiation, said means being further operative for creating in response to the application of infrared radiation to melt said surface, an opening in said body means through said surface.*

*43. A member according to claim 42*

*wherein the material of said meltable surface is black in color.*

*44. A member according to claim 41 or 42*

*wherein said wall means includes means for forming in said fluid passage a closed end portion, and*

*wherein said meltable surface is disposed generally adjacent to said closed end portion of said fluid passage.*

*45. An assembly for sealing and connecting the end portions of a pair of conduits, said assembly comprising*

*housing means having walls enclosing a hollow interior, said walls being made of a material having a first rate of absorption of electromagnetic radiant energy, said housing means further including spaced first and second passage means each communicating with said hollow interior and each adapted for communicating with a respective conduit end portion; and*

*meltable wall means extending across said hollow interior in the interval between said spaced first and second passage means, said meltable walls being made of a material having a second rate of absorption of electromagnetic radiant energy greater than said first rate and being operative for normally blocking flow communication between said first and second passage means through said hollow interior and for forming, in response to the application of electromagnetic radiant energy through said housing means walls to melt said meltable wall means, an opening establishing flow communication between said first and second passage means through said hollow interior.*

*46. A container comprising*

*wall means defining an interior,*

*means defining a port communicating with said interior, and*

*conduit means communicating with said port and including body means being made of a material which is generally transparent to the passage of electromagnetic radiant energy and means defining a meltable wall sealingly disposed on said body means and being made of a material which is generally opaque to the passage of electromagnetic radiant energy for normally sealing said port, and thus said container interior, and for forming, in response to the application for electromagnetic radiant energy melt said wall, an opening in said wall.*

*47. A container according to claim 46*

*and further including means for bringing said meltable wall into facing contact with a corresponding meltable wall associated with a second container having conduit means as defined by claim 46, and*

*wherein said opening in each of said meltable walls which is formed in response to said application of electromagnetic radiant energy is disposed generally along the point of facing contact between said meltable walls.*

*48. A container comprising*

*wall means defining an interior,*

*means defining a port communicating with said interior, and*

*conduit means communicating with said port and including body means being made of a material which is generally transparent to the passage of infrared radiation and means defining a meltable wall sealingly disposed on said body means and being made of a material which is generally opaque to the passage of infrared radiation for normally sealing said ort, and thus said container interior, and for forming in response to the application of infrared radiation to melt said wall, an opening in said wall.*

*49. A container according to claim 48*

*and further including means for bringing said meltable wall into facing contact with a corresponding meltable wall associated with a second container having conduit means as defined by claim 62, and*

*wherein said opening in each of said meltable walls which is formed in response to said application of infrared radiation is disposed generally along the point of facing contact between said meltable walls.*

*50. A container according to claim 47 or 49*

*wherein said meltable wall includes at said point of facing contact a generally outwardly bowed portion to facilitate said facing contact.*

*51. A container according to claim 46 or 48 wherein said meltable wall is made of material having a melting temperature of at least 200° C.*

*52. A blood collection system comprising*

*a blood collection subassembly for collecting blood from a donor,*

*a blood transfer subassembly for receiving a portion of the contents of said blood collection subassembly,*

*connector means communicating with each of said blood collection and said blood transfer subassemblies, each of said connector means including*

*means defining a meltable wall made of an electromagnetic radiant energy absorbing material for normally sealing said associated subassembly from communication with the atmosphere and for forming, in response to the application of electromagnetic radiant energy to melt said wall, an opening in said wall,*

*means for coupling said connector means associated with said blood collection subassembly with said connector means associated with said blood transfer subsassembly with said respective meltable walls in facing contact,*

*said meltable walls being further operative, in response to the application of electromagnetic radiant energy when said connector means are coupled together, for jointly melting to form a common opening defining a fluid path between said blood collection and transfer subassemblies.*

*53. A blood collection system according to claim 52*

*wherein the electromagnetic radiant energy applied includes infrared radiation, and*

*wherein the material of said meltable wall of each said connector means is generally opaque to the passage of infrared radiation.*

*54. A blood collection system according to claim 52 or 53*

*wherein said meltable wall of each of said connector means is made of material having a melting temperature of at least 200° C.*

* * * * *